US006447721B1

(12) United States Patent
Horton, III et al.

(10) Patent No.: US 6,447,721 B1
(45) Date of Patent: *Sep. 10, 2002

(54) DRINKING WATER UV DISINFECTION SYSTEM AND METHOD

(75) Inventors: Isaac B. Horton, III; Kurt Anthony Garrett, both of Raleigh, NC (US)

(73) Assignee: Remotelight, Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/723,679

(22) Filed: Nov. 28, 2000

Related U.S. Application Data

(63) Continuation of application No. 09/630,245, filed on Jul. 31, 2000.

(51) Int. Cl.⁷ .................................................. A61L 2/00
(52) U.S. Cl. ..................... 422/24; 250/450.11; 218/748
(58) Field of Search ....................... 422/24; 250/450.11; 210/748

(56) References Cited

U.S. PATENT DOCUMENTS

| | | | |
|---|---|---|---|
| 4,008,045 A | * | 2/1977 | Free |
| 5,501,801 A | * | 3/1996 | Zhang et al. ................ 210/748 |
| 5,751,870 A | * | 5/1998 | Forkner et al. ............... 385/33 |
| 5,780,860 A | | 7/1998 | Gadgil et al. |
| 5,857,041 A | * | 1/1999 | Riser et al. .................... 385/31 |
| 5,911,020 A | * | 6/1999 | Riser et al. .................... 385/33 |
| 5,992,684 A | | 11/1999 | Russell |
| 6,027,766 A | | 2/2000 | Greenberg et al. |
| 6,090,296 A | | 7/2000 | Oster |
| 6,094,767 A | | 8/2000 | Iimura |
| 6,103,363 A | | 8/2000 | Boire et al. |
| 6,110,528 A | | 8/2000 | Kimura et al. |
| 6,117,337 A | | 9/2000 | Gonzalez-Martin et al. |

* cited by examiner

*Primary Examiner*—Krisanne Thornton
(74) *Attorney, Agent, or Firm*—Glasgow Law Firm, PLLC

(57) ABSTRACT

An ultraviolet (UV) disinfection system and method for treating fluids including a configuration and design to function effectively with at least one UV light source or lamp that is not submerged in the fluid. The UV light source is positioned outside the fluid to be disinfected via exposure to at least one UV dose zone outside the fluid being treated wherein UV light is projected into the at least one dose zone. The UV light source may be presented in a vertical riser configuration, wherein the UV light source is positioned above the fluid to be treated and projecting a UV dose zone downward toward and into the fluid to be treated, with the fluid moving upward toward the UV light source. Alternatively, the UV light source may be presented in a non-vertical riser configuration, wherein the UV light source is positioned above the fluid stored at least temporarily within a reservoir and projecting a UV dose zone downward toward and into the static fluid to be treated, and is particularly effective where the fluid is pre-treated or purified drinking water.

72 Claims, 8 Drawing Sheets

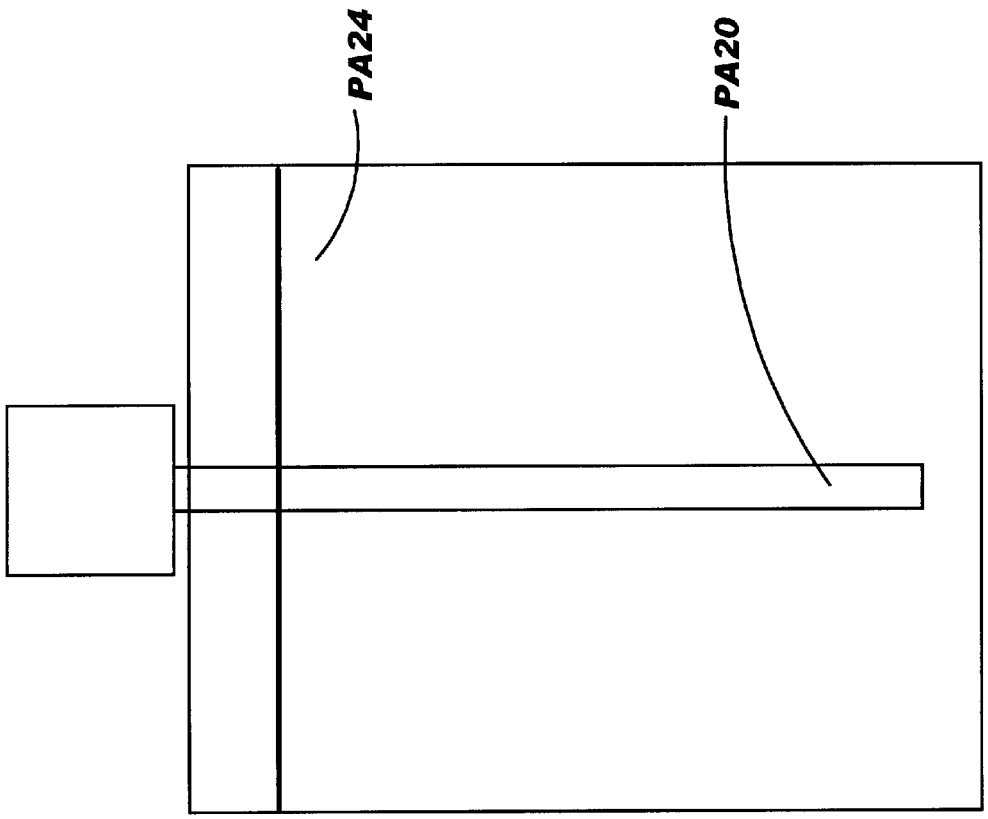

US 6,447,721 B1

DRINKING WATER UV DISINFECTION SYSTEM AND METHOD

CROSS-REFERENCE TO RELATED APPLICATIONS

This non-provisional utility patent application claims the benefit of one or more prior filed co-pending non-provisional applications; a reference to each such prior application is identified as the relationship of the applications and application number (series code/serial number): The present application is a Continuation of application Ser. No. 09/630,245, filed Jul. 31, 2000, which is incorporated herein by reference in its entirety.

BACKGROUND OF THE INVENTION

(1) Field of the Invention

The present invention relates generally to a system and method for ultraviolet disinfection and, more particularly, to a system and method for ultraviolet disinfection of drinking water.

(2) Description of the Prior Art

UV Mechanism of Action

It is well known in the art to use ultraviolet light (UV) for the disinfection treatment of water. Ultraviolet light, at the germicidal wavelengths, alters the genetic (DNA) material in cells so that bacteria, viruses, molds, algae and other microorganisms can no longer reproduce. The microorganisms are considered dead, and the risk of disease from them is eliminated. As the water flows past the UV lamps in UV disinfection systems, the microorganisms are exposed to a lethal dose of UV energy. UV dose is measured as the product of UV light intensity times the exposure time within the UV lamp array. Microbiologists have determined the effective dose of UV energy to be approximately about 34,000 microwatt-seconds/cm2 needed to destroy pathogens as well as indicator organisms found in water. Typical prior art disinfection systems and devices emit UV light at approximately 254 nm, which penetrates the outer cell membrane of microorganisms, passes through the cell body, reaches the DNA and alters the genetic material of the microorganism, destroying it without chemicals by rendering it unable to reproduce.

Ultraviolet light is classified into three wavelength ranges: UV-C, from about 200 nanometers (nm) to about 280 nm; UV-B, from about 280 nm to about 315 nm; and UV-A, from about 315 nm to about 400 nm. Generally, UV light, and in particular, UV-C light is "germicidal," i.e., it deactivates the DNA of bacteria, viruses and other pathogens and thus destroys their ability to multiply and cause disease, effectively resulting in sterilization of the microorganisms. Specifically, UV "C" light causes damage to the nucleic acid of microorganisms by forming covalent bonds between certain adjacent bases in the DNA. The formation of these bonds prevents the DNA codon from being read correctly for replication, and the organism is neither able to produce molecules essential for life process, nor is it able to reproduce. In fact, when an organism is unable to produce these essential molecules or is unable to replicate, it dies. UV light with a wavelength of approximately between about 250 to about 260 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

Regulation of Drinking Water Standards

Exposure to pathogens does not always cause disease; whether drinking contaminated water could produce disease depends on the type and quantity of pathogen ingested and the health (nutritional and immunological) status of the person drinking the water. After studying certain variables, including the species and number of pathogens, the World Health Organization (WHO) has determined a standard of performance that must be met by acceptable water disinfection systems. The standard requires that an acceptable water disinfection system must be able to process contaminated water with 100,000 CFUs (colony forming units) of *Escherichia coli* (*E. coli*) per 100 ml of water and produce outlet water with less than one CFU per 100 ml.

United States Environmental Protection Agency (EPA) standards, as set forth in the National Primary Drinking Water Regulations (NPDWRs), have specific requirements for the levels of certain bacteria, protozoa, and viruses. *Giardia lamblia*, a protozoon, and all viruses must be 99.9% killed or inactivated. Heterotrophic microorganisms cannot exceed 500 colony-forming units (CFUs) per ml. No more than 5.0% of samples can be total coliform-positive in a month, and there can be no fecal coliforms present. Fecal coliforms and *E. coli* are bacteria whose presence indicates that the water may be contaminated with human or animal wastes. Microbes in these wastes can cause diarrhea, cramps, nausea, headaches, or other symptoms.

Prior Art

Typically, prior art devices and systems for disinfecting water via ultraviolet light exposure commonly employ standard ultraviolet light sources or lamps encased in quartz sleeves and suspended in the water being treated. Benefits of using ultraviolet light for disinfecting water include the following: no chemicals, like chlorine, are needed to ensure effective water disinfection provided that the proper number of lamps are used and properly positioned for a given influent and flow rate; since no chemicals are required in the disinfection process, no storage and/or handling of toxic chemicals is required; no heating or cooling is required to ensure disinfection; no storage tanks or ponds are necessary because the water can be treated as it flows through the system; no water is wasted in the process; no change in pH, chemical or resistivity of the water being treated; approximately at least 99.99% of all waterborne bacteria and viruses are killed via UV light exposure for disinfection; thereby providing increased safety of using the system and effectiveness of same.

As set forth in the foregoing, prior art UV water treatment systems disinfect and remove microorganisms and other substances from untreated, contaminated water sources and produce clean, safe drinking water. The core technology employed in WaterHealth International's system includes a patented, non-submerged UV light. This technology is claimed by WHI to be a recent and tested innovation developed at the Lawrence Berkeley National Laboratory, a premier, internationally respected laboratory of the U.S. Department of Energy managed by the University of California. This prior art system delivers a UV dose of up to 120 mJ/cm$^2$, which is more than three times the NSF International requirement of 38 mJ/cm$^2$ and exceeds World Health Organization and EPA water quality standards and effectively treats bacteria, viruses and Cryptosporidium in drinking water. In addition, recent research conducted at two different laboratories indicates that UV doses of 10 mJ/cm$^2$ or less produce 4-log reductions in Giardia. Based on this research, UV dosage of up to 120 mJ/cm$^2$ greatly exceeds the dosage required for inactivation of Giardia. Additional components included in WaterHealth International's systems effectively treat specific problems such as turbidity, silt, tastes, odors and various chemicals.

The UV light source used in prior art are typically low pressure mercury lamps, which can effectively clean water of dangerous and illness-causing viruses and bacteria, including intestinal protozoa such as Cryptosporidium, Giardia, and E. coli, provided that the proper number and configuration of lamps are included in the system.

Prior art UV disinfectant systems work best when the water temperature is between about 35 and about 110 degrees Fahrenheit, since extreme cold or heat will interfere with the UV system performance. Home temperatures are typically in this range.

Among applications for UV disinfection systems for water include the beverage industry, wastewater treatment, and surface treatment. By way of example and explanation, hot filled beverages, cold filled beer and other sensitive drinks are susceptible to contaminants introduced by the liners of closures. Mold is of particular concern since packaging headspace frequently contains low levels of oxygen. Medium pressure UV inactivates mold spores to prevent this problem, including contamination of beverages during production and storage, which can cause discoloration, unusual taste or bad flavor, and reduced shelf life. UV disinfection systems solve these issues by eliminating problem microorganisms without adding chemicals or heat. Disinfection of municipal water using UV light avoids problems associated with storage, transport and use of chemicals and associated regulation for them. Ultraviolet light can help improve shelf life of products and allow processors to reduce chemical additives in wash water without sacrificing high levels of disinfection. UV light provides non-chemical microbial control for captive water loops without altering the taste, color or odor of the food. Environmentally safe UV disinfection is one of the few water treatment methods unburdened by regulatory restrictions, consumer/environmental group concerns or high operation costs.

Problems Associated with Prior Art

Generally, UV disinfection is a safe and reliable means for disinfecting drinking water for daily use, particularly given its relatively rapid, inexpensive, non-taste and odorless resultant water. UV light is a World Health Organization-approved method of disinfecting drinking water (Guidelines for Drinking Water Quality, vol. 1, World Health Organization, Geneva, Switzerland, 1993, p. 135). However, UV disinfection is not generally recommended for long-term storage of water. Although UV disinfection will reduce pathogen levels to an acceptable level, a miniscule quantity of microbial contaminants may not be sterilized by the UV irradiation. Once the UV irradiation treatment is terminated, microbes that have survived the sterilization process may be able to replicate. Therefore, an ongoing disinfection system is required for longterm storage of water and other fluids. The most common means of maintaining water at an acceptable purity for long periods of time is through the addition of reactive chlorine. Unfortunately, evidence is mounting that organic chemical byproducts of chemical disinfection, especially byproduct of chlorination such as dioxane, are carcinogens and/or toxins for humans. Therefore, chemical disinfection is not a viable alternative when chemical purity of the fluid is desired and/or required. Additionally, in spite of this toxicological evidence, the EPA has recently been forced to relax restrictions on certain known carcinogenic chlorination by-product, such as chloroform. Additionally, other chemicals, such as the nitrate ion, have been shown to negatively influence the development of children.

In light of the emerging data concerning the toxicity of organic and inorganic chemicals and the relaxation of water purity regulations, persons interested in maintaining their health have been pursuing the supply of chemically pure water. Generation of such water requires filtration to remove the chemicals. Unfortunately, systems based on filtration require frequent replacement and/or cleaning of filters. In addition, storage of such water requires a system to maintain sterility for extended periods of time. Thus, there exists a need for a system that can easily remove or eliminate organic compounds from drinking water and maintain the sterility of that water during storage.

Current UV sterilization systems employ a submerged UV light system. Disadvantageously, a submerged UV light system requires cleaning and maintenance of the exterior of the system in order to protect the UV lamp or light source used in nearly all prior art systems. This cleaning can become a time-consuming duty, especially when working with multi-lamp low-pressure systems. During operation while the UV lamps and surrounding quartz sleeves are suspending in the water to be treated, minerals and contaminants in the water deposit onto the quartz sleeves, thereby causing fouling on the sleeve surface. This fouling reduces the effectiveness of the UV lamps because the fouling interferes with the UV light transmission into the water. To save time and prevent quartz sleeve fouling a cleaning mechanism can be supplied for either manual or automatic operation, like using wiper glides over the sleeves to remove deposits, which may block the light emitted from the UV lamp. This provides improved performance and reduces maintenance time, but only where the water quality is low. In every case, the UV lamps encased in quartz sleeves must be removed for cleaning on at least a monthly basis, depending on specifics of a given system and its influent and flow rates. The cleaning requires the system to be shut down temporarily or diverted to other UV lamps, so system shut down decreases capacity and/or increases operating costs. Also disadvantageously, UV lamps are susceptible to breakage, and if submerged, can contaminate the surrounding water. Commercially, only WaterHealth, Inc., might in any way suggest the use of non-submerged lamps for UV systems but these are limited expressly in advertising literature as applicable only and exclusively in applications that do not require high purification, e.g., previously purified drinking water but not surface water, aquifer water, wastewater, or otherwise unpurified water treatment applications.

These prior art systems do not employ optical components nor reflective materials or photocatalytic materials in the holding tank and reaction vessels.

Thus, there remains a need for a UV disinfection system for treating fluids having reduced maintenance time and costs, increased flow rates for a given disinfection level, lower overall equipment, installation, and system costs, reduced risk of fluid contamination by equipment breakage, and capable of maintaining the sterility of fluids for extended storage periods. Additionally, there remains a need for water purification system that can remove or degrade organic compounds and other chemical contaminants in fluids with reduced maintenance.

SUMMARY OF THE INVENTION

The present invention is directed to a UV disinfection system and method for treating fluids, particularly water, whereby the UV light source requires less maintenance and cost than prior art systems and devices while providing at least the same disinfection level for a given influent and flow rate thereof.

One object of the present invention is to provide a UV disinfection system for treating fluids configured and arranged to function effectively with at least one UV light source or lamp that is not submerged in the fluid to be disinfected. The UV light source is positioned outside the fluid to be disinfected via exposure to at least one UV dose zone wherein UV light is projected into the zone.

Another object of the present invention includes presentation of the UV light source presented in at least two primary configurations: a vertical riser configuration and a non-riser, holding tank configuration. In the vertical riser configuration the UV light source is positioned above the fluid to be treated and projecting a UV dose zone downward toward and into the fluid to be treated, with the fluid moving upward toward the UV light source. Alternatively or in series combination with the vertical riser configuration, the UV light source maybe presented in a non-riser, holding tank configuration, wherein the UV light source is positioned above the fluid holding tank or other container to be treated and projecting a UV dose zone downward toward and into the fluid to be treated, with the fluid in a substantially static or non-moving conditions.

Still another object of the present invention is to provide a UV dose zone including at least one zone, more preferably four zones, wherein one zone includes an interface zone positioned between the UV light source and the fluid to be treated and another zone includes a reaction zone positioned within the fluid. The reaction zone may be formed by an interface plate that incorporates catalytic properties to enhance desired reactions.

The present invention is further directed to a method for treating fluids by disinfecting those fluids using UV light projected by at least one UV light source producing at least one dose zone, the UV light source being positioned outside the fluid.

Accordingly, one aspect of the present invention is to provide a system and method for disinfecting fluid including at least one UV light source positioned outside the fluid to be treated with the at least one UV light source producing at least one UV dose zone for disinfecting the fluid, wherein the fluid is water, preferably water that has been previously treated for sterilization and/or disinfection.

Another aspect of the present invention is to provide a system and method for disinfecting and purifying fluid including at least one UV light source positioned outside the fluid to be treated with the at least one UV light source producing four UV dose zones for disinfecting the fluid, with one zone provided at an interface zone, and one zone provided at a reaction zone positioned between the UV light source and the fluid to be treated. The reaction zone may be formed by an interface plate that incorporates catalytic properties to enhance desired reactions Still another aspect of the present invention is to provide a system and method for disinfecting fluid including at least one UV light source positioned outside the fluid to be treated with the at least one UV light source producing at least one UV dose zone for disinfecting the fluid, wherein the at least one UV light source is a medium-to-high intensity UV light source or spectral calibration lamp. These and other aspects of the present invention will become apparent to those skilled in the art after a reading of the following description of the preferred embodiment according to the present invention when considered with the drawings.

BRIEF DESCRIPTION OF THE DRAWINGS

FIG. 1B is an illustration of other PRIOR ART in a side view.

DETAILED DESCRIPTION OF THE PREFERRED EMBODIMENTS

Figure 1A:
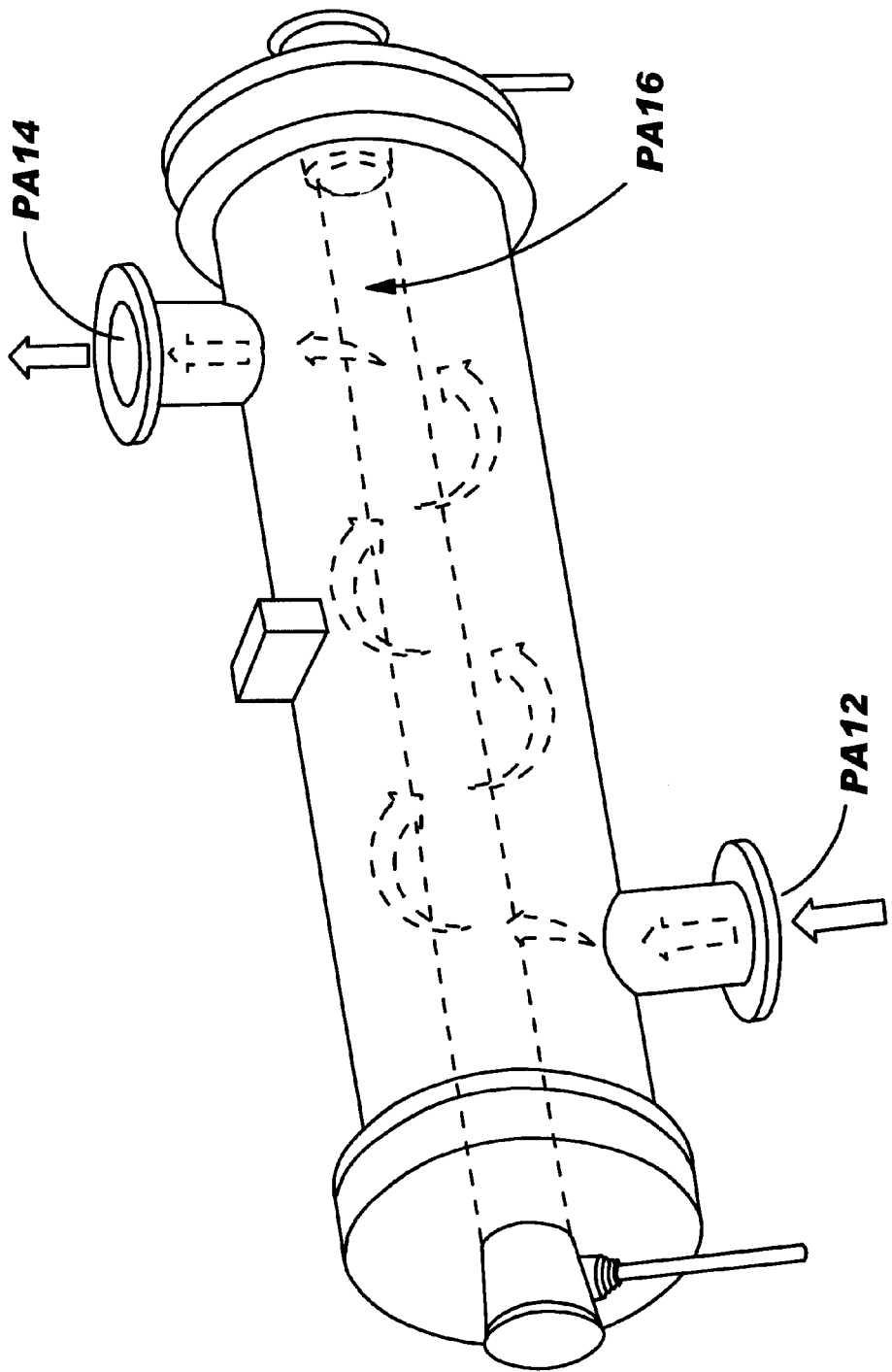
FIG. 1A is an illustration of PRIOR ART in a side view.

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms.

Referring now to the drawings in general, the illustrations are for the purpose of describing a preferred embodiment of the invention and are not intended to limit the invention thereto. FIG. 1A shows a prior art UV fluid disinfection system that includes a submerged UV lamp configuration PA16 around which fluid to be treated flows. The fluid enters through an inlet PA12, flows around the UV lamp PA16, and exits the system through an outlet PA14. FIG. 1B shows a prior art UV fluid disinfection system that includes a submerged UV lamp configuration PA20 surrounded by a substantially static or non-flowing fluid PA24. Disadvantages of the prior art systems as set forth in the foregoing background section include high maintenance time and costs, low flow rates for a given disinfection level, high overall equipment, installation, and system costs, and high risk of fluid contamination by equipment breakage.

By contrast to prior art, the present invention is directed to an ultraviolet (UV) disinfection system and method for treating fluids including a configuration and design to function effectively with at least one UV light source or lamp that is not submerged in the fluid. Advantageously, the non-submerged configuration of the present invention prevents the problems associated with breakage of the lamp and/or lamp housing and fouling of the lamp housing. Additionally, the non-submerged configuration of the present invention prevents the problems associated with extreme temperatures in the fluid. Fluorescent lamps, including UV lamps, lose a significant amount of output at low temperatures. Thus, a non-submerged system, which separates the lamp from the fluid to be treated, allows for the temperature of the lamp to be maintained at more optimal temperature, without necessitating cooling or heating the fluid as well. Thus, this system more efficiently disinfects extreme environments, such as freezers, coolers, hot water heaters, and the like.

Vertical Riser Configuration (VRC)

Figure 2:
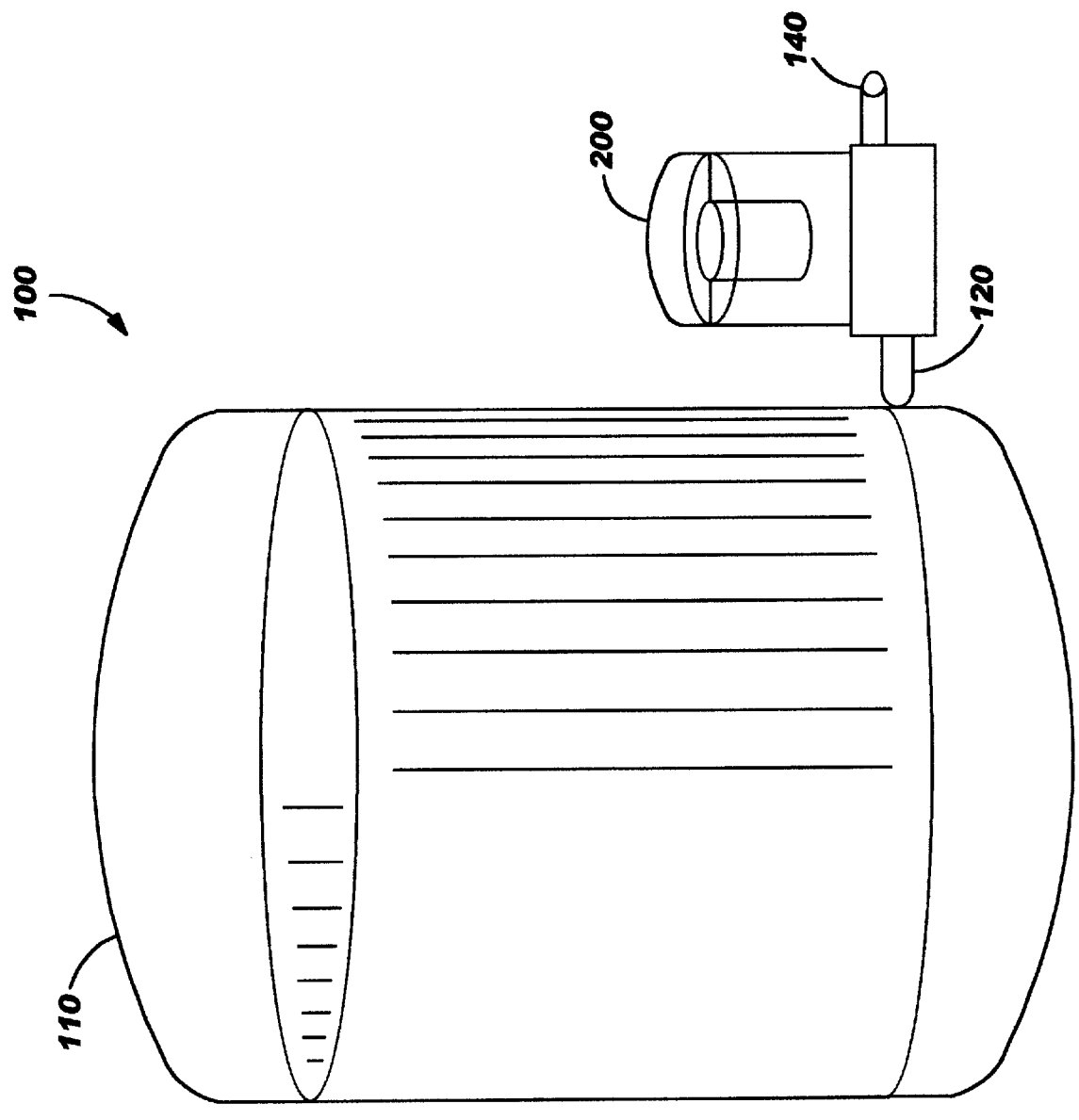
FIG. 2 is an illustration of a side view of a UV disinfection system constructed according to the present invention in a vertical riser configuration.
Figure 3:
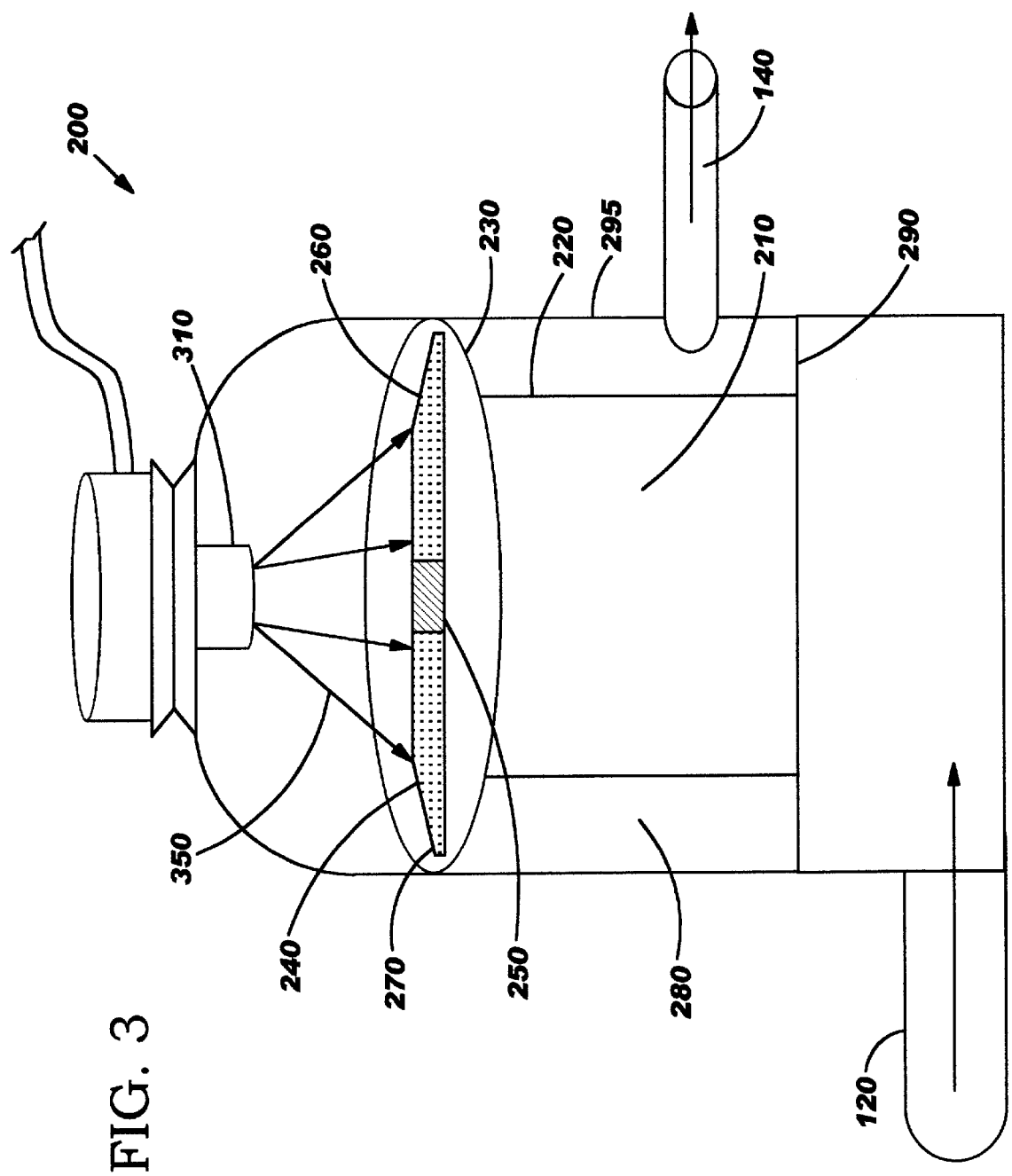
FIG. 3 is an illustration of an exploded side view of the embodiment shown in FIG. 2.

The UV light source may be presented in a vertical riser configuration according to a preferred embodiment of the present invention, as shown generally at 100 in FIG. 2, wherein the fluid exits a reservoir or holding container 110 via a pipe or outlet 120 into the vertical riser configuration (VRC) 200 and passes therethrough prior to discharge from the pipe or outlet 140 for consumption or end use. Preferably, the fluid is a pretreated water that has already been disinfected and purified, possibly with low total dissolved solids therein. Furthermore, the VRC, as shown generally at 200 in FIG. 3, includes at least one UV light source 310. This UV light source 310 is part of a lamp assembly, as shown generally at 300 in FIG. 5. The lamp assembly 300 is composed of a housing 320 that encases the UV light source 310, UV light rays 330, at least one optical component 340, and UV light ray output 350 that exits the housing. Referring to FIG. 3, the UV light ray output 350 exits the housing above the fluid 210 to be treated, this fluid entering the VRC from the outlet pipe 120 of the holding container or reservoir 110 and being forced upward through the interior pipe 220 of the VRC 200 toward the UV light ray output 350 that is projected downward toward the fluid surface 230 and into the fluid 210 to be treated, once again with the fluid moving upward toward the UV light source 310. At least one interface plate 240 may be fitted to the top of the interior pipe 220, thus increasing the exposure time of the fluid 210 to the UV light ray output 350. The at least one interface plate 240 contains a hole or holes 250 that allows fluid rising upward through the interior pipe 220 to exit at the top of the pipe. The fluid then traverses across the superior surface 260 of the interface plate 240 to the plate edge 270, where it then descends into the exterior chamber 280 of the VRC. The fluid is prevented from returning into the interior pipe 220 by a base plate 290 that solidly connects the exterior of the interior pipe 220 with the interior of the outer pipe 295. The fluid then exits the VRC 200 through the pipe or outlet 140. The UV light rays 330 may be projected downward from a UV light source or a lamp system 310 that includes optical components. These optical components may include, but are not limited to, reflectors, shutters, lenses, splitters, focalizers, mirrors, rigid and flexible light guides, homogenizer or mixing rods, manifolds and other couplers, filters, gratings, diffracters, color wheels, and the like. These optical components are internal to the lamp system and are positioned between the UV light source or lamp 310 and the UV ray light output 350 of the lamp assembly 300, thereby focusing, directing, and controlling the light ray output 350 that irradiates the fluid 210 and that sterilizes any microorganisms that exist in the fluid 210. The UV light ray output 350 irradiates and may also be transmitted through the fluid 210. UV light ray output 350 that is transmitted through the fluid and strikes the reflective interior surfaces (not shown) of the VRC components is reflected back into the fluid where it may strike microorganism. The reflection of the UV light ray output 350 back into the fluid by the reflective interior surfaces of the VRC components enhances the killing capacity of the VRC system 200.

Additionally, the interface plate may possess catalytic properties such that certain reactions are catalyzed in the vicinity of the interface plate. For example, $TiO_2$ may be incorporated into the interface plate that is made of glass or other appropriate material. When such a plate is irradiated with catalyst-activating wavelengths, fatty acids and other organic chemicals are chemically reduced, resulting in degradation to smaller volatile products such as methane, ethane, etc. Additionally, nitrate ion is reduced to elemental nitrogen in such a system. Thus, the incorporation of $TiO_2$ into the interface plate with subsequent UV irradiation reduces the levels of two potential human toxins - organic chemicals and nitrate ion.

In addition, the interface plate may induce turbulence or cause fluid cascade with a non-planar surface, stair-step surface, downwardly sloping surface, or other the like. The induction of turbulence is particularly advantageous when the fluid is turbid. Turbidity, which is the state of water when it is cloudy from having sediment stirred up, interferes with the transmission of UV energy and decreases the disinfection efficiency of the UV light disinfection system. Thus, turbulence, by inducing rotation in the particle, causes all aspects of a particle to be exposed to the UV light. Additionally, the photocatalytic properties of the system reduce turbidity by degrading the compounds or particles responsible for the turbidity. Furthermore, the reflective aspects of the surfaces of the system enhance the efficacy of the system when operated under turbid conditions because the UV light can strike the various aspects of a particle with the need for the particle to be rotating, thus overcoming the opacity of the particle. Another aspect that enhances performance under turbid conditions is the high UV light intensity of the system. The high UV light intensity can more easily compensate for fluctuations in turbidity than lower-intensity systems. Thus, the preferred embodiment has several characteristics which enhance its performance under turbid conditions.

In cases where the water has high iron or manganese content, is clouded and/or has organic impurities, it is usually necessary to pre-treat the water before it enters the UV disinfection stage because deposits on the quartz-encased submerged UV lamps, which are immersed in the water to be treated, interfere with the UV light transmission, thereby reducing the UV dose and rendering the system ineffective. Prior art typically employs UV purification in conjunction with carbon filtration, reverse osmosis and with certain chemicals to reduce fouling between cleanings of the quartz sleeves that surround the UV lamps. Thus, another advantage of the preferred embodiment is that turbidity reduction is not necessary for the system to perform adequately, and thus the system eliminates the need for expensive pre-treatment of the fluid to reduce turbidity.

Advantageously, the disinfected, purified water that exits the total system from the VRC device is completely free from microorganisms without requiring the addition of chemicals or other additives that would increase the total dissolved solids in the water. Thus, the disinfection process according to the present invention has not changed the taste, pH, resistivity, and other characteristics of the exiting water.

Another factor in the design of a UV disinfection system and method according to the present invention where the VRC is used involves the integration of two main components, including the non-submerged UV light source system and the hydraulic system. The light source system includes a housing surrounding and supporting a UV light source or lamp having at least one optical component positioned and arranged to direct the UV light rays toward and through an output, thereby introducing UV light rays toward a fluid for disinfection of the fluid.

The hydraulic system includes a hydraulic tube and pumping system for forcing the fluid upward through the tube toward the light source(s). The present invention includes the use of hydraulic systems that comprise a transporter or pumping system, and at least one interface plate. The hydraulic system serves at least three functions: it carries water influent to an interface and provides flow to at least one interface plate and discharges the treated influent water to a reservoir or water system. The VRC system may include quick-connect lamps and housings with a monitoring and indicator system that would indicate that a lamp had failed. Each riser in the VRC system may have an individual, dedicated lamp and optical system with overlap between neighboring lamps to eliminate dead zone. Each riser in the VRC system may also have a valve that shuts off the riser in case of failure.

Non-Riser Configuration

Figure 4:
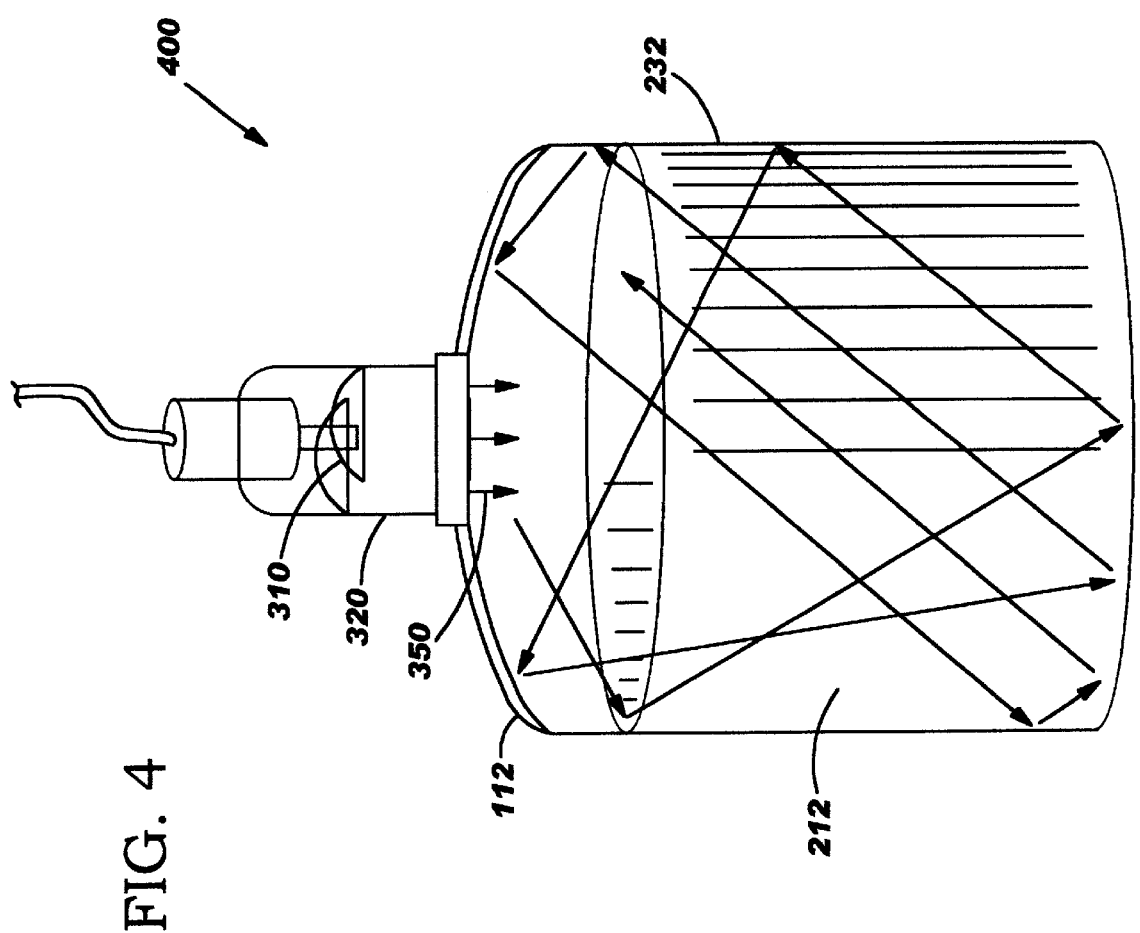
FIG. 4 shows an illustration of a UV disinfection system of an alternative embodiment of the present invention.
Figure 5:
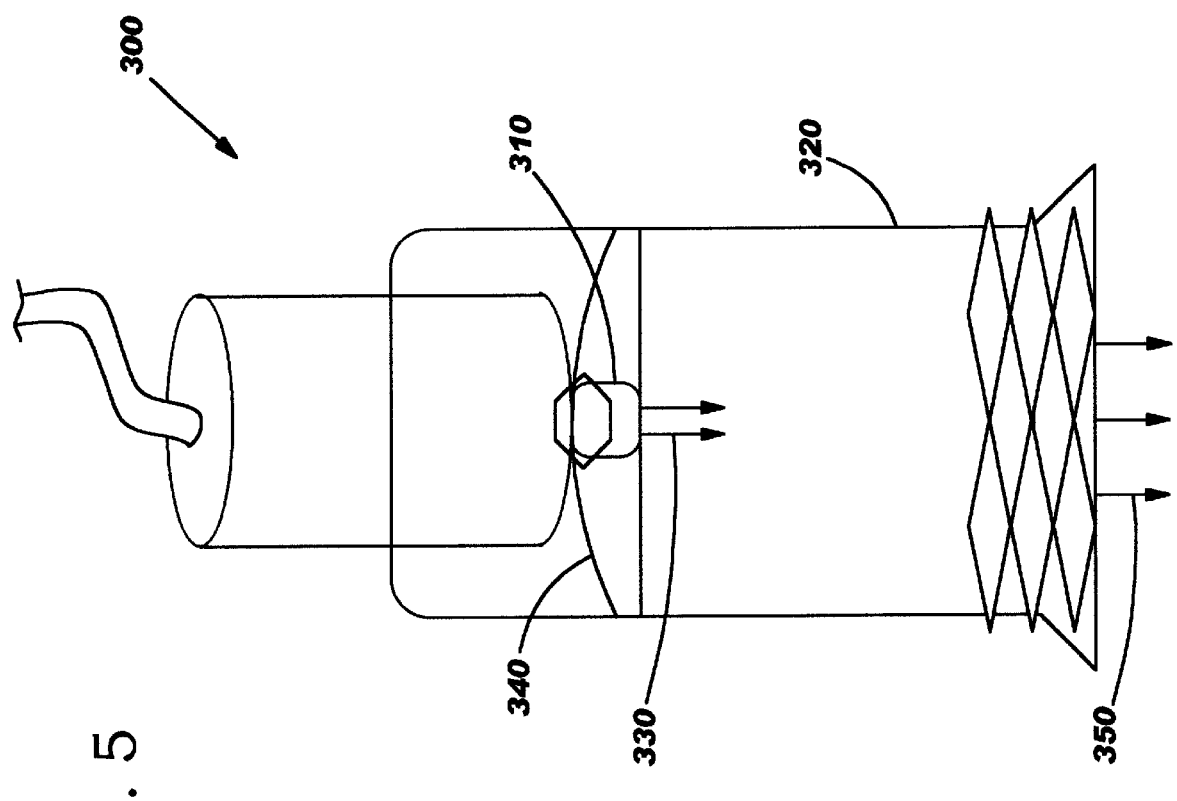
FIG. 5 is an illustration of an exploded side view of the embodiment shown in FIG. 4.

Alternatively or in combination with the VRC system, a non-VRC configuration is advantageously constructed and configured to provide UV disinfection from a non-submerged UV light source for a reservoir, holding container, or other non-flowing water storage, however temporary the water dwell time may be. Preferably, the fluid is pre-treated water that has already been disinfected and purified, possibly with low total dissolved solids therein. This pretreatment may have occurred in a VRC system that incorporates a catalytic plate to reduce organic and inorganic contaminants in the water, in addition to disinfecting the water. As illustrated in FIGS. 4 & 5, the present invention, generally referenced 400, is a non-riser configuration (NRC) that includes at least one UV light source 310. This UV light source 310 is part of a lamp assembly, as shown generally at 300 in FIG. 5. The lamp assembly 300 is composed of a housing 320 that encases the UV light source 310, UV light rays 330, at least one optical component 340, and UV light ray output 350 that exits the housing. Additionally, the light source is connected to a timer, which permits the activation and/or deactivation of the light source at a predetermined time, e.g., after the light source has been activated or ON for a period of time adequate to sterilize the entire reservoir or container, as well as after the light source has been activated or ON for a period of time. Referring to FIG. 4, the UV light ray output 350 exits the housing 320 above the substantially static fluid 212 to be treated, this fluid being held in a holding container or reservoir 112 and not being forced toward UV light ray output 350 that is projected downward toward the fluid surface 232 and into the fluid to be treated 212, once again with the fluid 212 not being forced toward the UV light source 310. The UV light ray output 350 may be projected downward from a UV light source or a lamp system 300 that includes optical components as previously described. These optical components may include, but are not limited to, reflectors, shutters, lenses, splitters, focalizers, mirrors, rigid and flexible light guides, homogenizer or mixing rods, manifolds and other couplers, filters, gratings, diffracters, color wheels, and the like. These optical components are internal to the lamp system and are positioned between the UV light source or lamp 310 and the UV ray light output 350 of the lamp system 300, thereby focusing, directing, and controlling the light ray output 350 that irradiates the fluid 212 and that sterilizes any microorganisms that exist in the fluid 212. The UV light ray output 350 irradiates and may also be transmitted through the fluid 212. UV light ray output 350 that is transmitted through the fluid and strikes the reflective interior surface of the holding tank or container 112 is reflected back into the fluid where it may strike microorganism. The reflection of the UV light ray output 350 back into the fluid by the reflective interior surface of the holding tank or container 112 enhances the killing capacity of the NRC system 400.

Advantageously, both systems have several UV dose zones established within them. In the VRC system, as best shown in FIGS. 3 and 5, the UV light source 310 is positioned within a UV light source system 300, including optical components as previously described, above the fluid to be treated and projecting a UV dose zone downward toward and into the fluid to be treated, with the fluid moving from the influent point 120, flowing vertically up the interior pipe 220 toward the UV light source 310, and then exiting the interior pipe 220 through the interface plate 240. The at least one UV light source is positioned above the fluid to be treated and projecting UV light ray output 350 downward toward and into the fluid to be treated, with the fluid moving upward toward the UV light source. Several UV dose zones are established within the VRC system, generally shown as 500 in FIG. 6. The first zone is the light source system exit UV dose zone 510, which occurs at the light source system and air interface. Then next zone is the air UV dose zone 520, which occurs just beneath the UV light source and just above the water and the at least one interface zone or plate 240. The next zone is the vapor zone 525, which occurs just above the water surface. The next zone is the interface zone UV dose zone 530, which occurs at the intersection of the water and the at least one interface zone or plate 240. The at least one interface plate is used to provide a reaction zone for UV disinfection of fluid flowing over the plate and to provide additional treatment means for balancing pH, affecting effluent chemistry, providing a catalyst, and the like. For example, $TiO_2$ may be incorporated into the interface plate to effect reduction of ions and compounds. Specifically, $TiO_2$ is used to reduce nitrates and nitrites to elemental nitrogen. Such a treatment is desirable, in that nitrates have been linked to developmental defects in children. Additionally, $TiO_2$ incorporated in glass or other suitable material and irradiated with catalyst-activating wavelengths will degrade fatty acids and other organic compounds adjacent to exterior of the glass. Thus, such a plate can be used to degrade organic contaminants found in water. Additionally, catalyst-activating wavelengths can catalyze a variety of reactions, and the use of these wavelengths with any one or combination of the plethora of available chemical catalyst generates numerous possible catalytic combinations that are used to catalyze a myriad of desirable reactions. The photocatalyst may include photo-activated semiconductors such as Titanium Oxide; TiO2 (photo activation wavelength; not more than 388 nm), Tungsten Oxide, WO2 (photo activation wavelength; not more than 388 nm), Zinc Oxide; ZnO (photo activation wavelength; not more than 388 nm), Zinc Sulfide; ZnS (photo activation wavelength; not more than 344 nm) and Tin Oxide; SnO2 (photo activation wavelength; not more than 326 nm), In addition to these catalysts, other catalysts, such as $PtTiO_2$, are known.

TiO2 may be preferably applied as the photocatalyst, considering that the activation power is very high, the catalyst is long-lived with high durability, and safety for human applications is certified, as TiO2 has been used safely for a long time in cosmetic and food applications. Additionally, the interface plate may be a biofilter, and contain enzymes or bacteria that react with substrates contained in the fluid.

Figure 6:
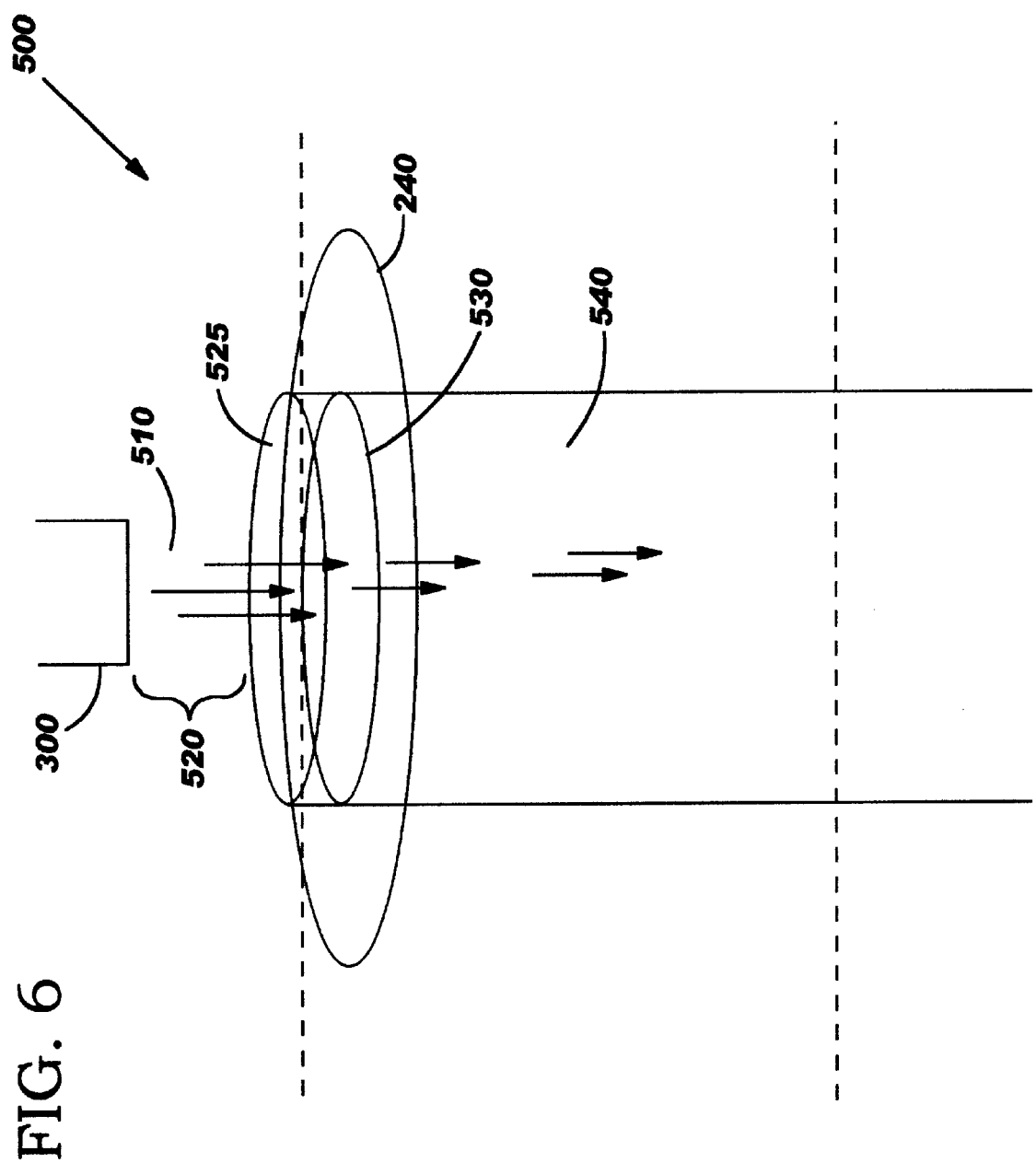
FIG. 6 is an illustration of the UV dose zones generated in a vertical riser configuration.

The last zone shown in FIG. 6 is the submerged UV dose zone 540, which creates a variable UV dose zone that decreases in effectiveness at greater distances from the UV light source.

Figure 7:
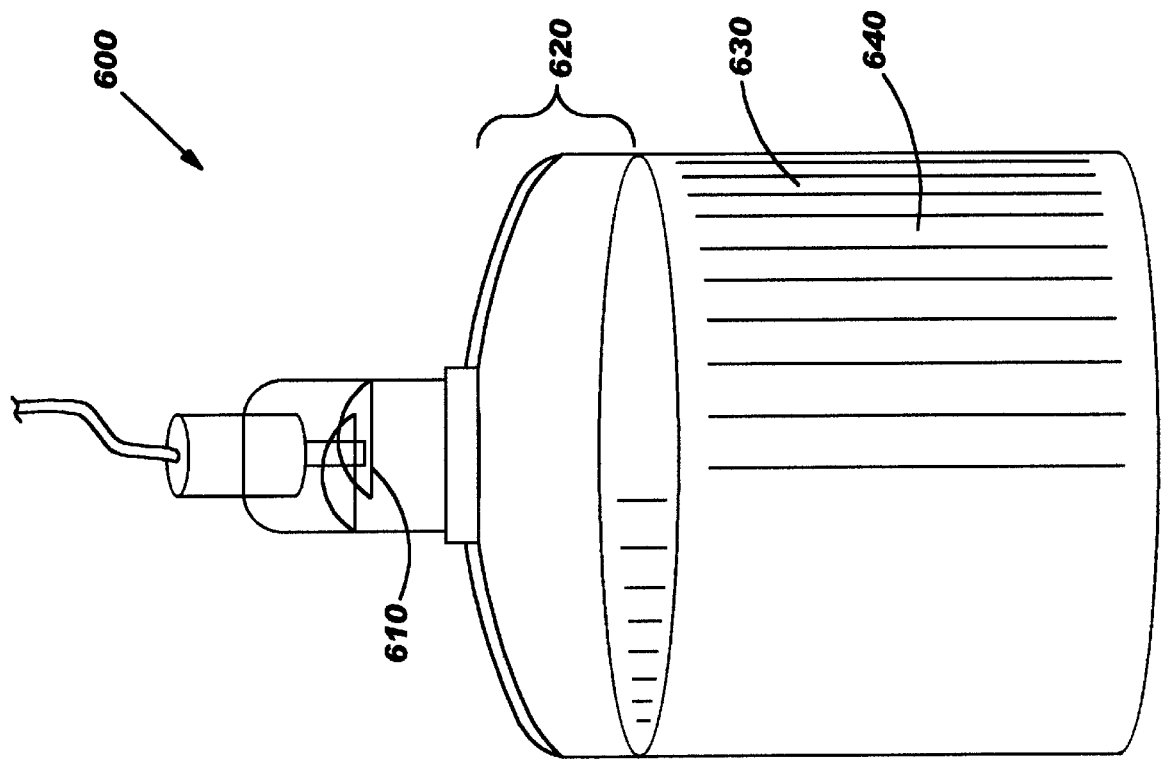
FIG. 7 is an illustration of the UV dose zones generated in an alternative embodiment of the present invention.

For the generally static non-riser configuration, the zones are different than those described in the VRC system. In the generally static non-riser system, generally shown as 600 in FIG. 7, the first zone is the light source system exit UV dose zone 610, which occurs at the light source system and air interface. Then next zone is the air UV dose zone 620, which occurs just beneath the UV light source and just above the water surface 230. The next zone is the vapor zone 630, which occurs just above the surface of the water. The last zone is the submerged UV dose zone 640, which creates a variable UV dose zone that decreases in effectiveness at greater distances from the UV light source.

While generally regarding the UV light source and configuration thereof, the preferred embodiment of the present invention includes at least one optical component positioned between the UV light source and the UV light source system output point. Advantageously, the use of optical components enables the system to maximize the intensity, focus, and control of the UV light rays at the output for any given UV light source or lamp. Also, optical components, including but not limited to reflectors, shutters, lenses, splitters, mirrors, rigid and flexible light guides, homogenizer or mixing rods, manifolds and other couplers, filters, color wheels, and the like, can be utilized in combination to achieve the desired control and output, as set forth in U.S. Pat. Nos. 6,027,237; 5,917,986; 5,911,020; 5,892,867; 5,862,277; 5,857,041; 5,832,151; 5,790,725; 5,790,723; 5,751,870; 5,708,737; 5,706,376; 5,682,448; 5,661,828; 5,559,911; D417,920 and co-pending applications Ser. Nos. 09/523,609 and 09/587,678 which are commonly owned by the assignee of the present invention, and which are incorporated herein by reference in their entirety. Additionally, optical component such as gratings, dichroic filters, focalizers, gradient lenses, and off-axis reflectors may be used.

With regard to light guides, these may be fiberoptic lines composed of acrylic, glass, liquid core, hollow core, core-sheath, or a combination.

With regard to lenses, several embodiments are envisioned. Imaging lenses, such as a parabolic lens, and non-imaging lenses, such as gradient lenses, may be used. A gradient lens collects light through a collecting opening and focuses it to an area smaller than the area of the collecting opening. This concentration is accomplished by changing the index of refraction of the lens along the axis of light transmission in a continuous or semi-continuous fashion, such that the light is "funneled" to the focus area by refraction. An example of gradient lens technology is the Gradium® Lens manufactured by Solaria Corporation. Alternatively, a toroidal reflector, as described in U.S. Pat. No. 5,836,667, is used. In this embodiment, a UV radiation source, such as an arc lamp, is located at a point displaced from the optical axis of a concave toroidal reflecting surface. The concave primary reflector focuses the radiation from the source at an off-axis image point that is displaced from the optical axis. The use of a toroidal reflecting surface enhances the collection efficiency into a small target, such as an optical fiber, relative to a spherical reflecting surface by substantially reducing aberrations caused by the off-axis geometry. A second concave reflector is placed opposite to the first reflector to enhance further the total flux collected by a small target.

Additionally, more than one reflector may be used with a lamp. For example, dual reflectors or three or more reflectors, as taught in U.S. Pat. Nos. 5,706,376 and 5,862,277, may be incorporated into the preferred embodiment. These reflectors may also be splitting reflectors and/or cascading reflectors.

In general, the transmissive optical components are UV transmissive and the reflective optical components are UV reflective. Additionally, any of the optical components, including the housing, may be made of acrylic or similar materials that degrade over time when exposed to UV light. These components can be replaced when their performance has deteriorated to an unacceptable level.

Notably, any number of lamps including low pressure, medium pressure, high pressure, and ultra high-pressure lamps, which are made of various materials, e.g., most commonly mercury (Hg) can be used with the system configuration according to the present invention, depending upon the fluid or influent characteristics and flow rates through the system. Furthermore, while high and ultra high pressure lamps have not been used commercially to date by any prior art system, predominantly because of the low energy efficiency associated with them and the lack of capacity for prior art design and configuration formulas to include high pressure UV lamps, the present invention is advantageously suited to accommodate medium to high to ultra high pressure lamps, all of which can be metal, halogen, and a combination metal halide. Additionally, spectral calibration lamps, electrodeless lamps, flashlamps, and pulsed lamps can be used.

In particular, a preferred embodiment according to the present invention employs a pencil-type spectral calibration lamp. These lamps are compact and offer narrow, intense emissions. Their average intensity is constant and reproducible. They have a longer life relative to other high wattage lamps. Hg (Ar) lamps of this type are generally insensitive to temperature and require only a two-minute warm-up for the mercury vapor to dominate the discharge, then 30 minutes for complete stabilization.

A Hg (Ar) UV lamp, which is presently commercially available and supplied by ORIEL Instruments, is used in the preferred embodiment according to the present invention. The ORIEL Hg(Ar) lamp, model 6035, emits UV radiation at 254 nm. When operated at 15 mA using a DC power supply, this lamp emits 74 microwatt/cm2 of 254 nm radiation at 25 cm from the source.

The system according to the present invention uses UV lamps configured and functioning above the fluid or water flow, not immersed in the fluid flow as with all prior art systems designed for use in all water treatment applications. With this system, the number of lamps necessary to treat a given influent and flow rate can be reduced by perhaps a factor of ten, which is a major advantage in practical application. Also, the lamps are not susceptible to fouling, since they are not immersed in the fluid to be disinfected. Additionally, the design of the present invention allows for a significant reduction in heat in the water. Furthermore, the maintenance and servicing is greatly simplified. Also, in the vertical riser configuration according to one preferred embodiment configuration according to the present invention, the reactor design, which would comprise a number of cylindrical tubes oriented vertically, includes a hydraulic system having pumping equipment and a significant amount of pumping power. Furthermore, the present invention is an optical UV light source system for use in a fluid disinfection system. As such, traditional mathematical models used for determining energy efficiencies for the present invention are inadequate and inapplicable. Thus, given the use of optical components associated with the UV light source, the use of medium to ultra high pressure UV lamps, and the introduction of at least one UV dose zone existing outside the water to be treated, the present system presents a revolutionary approach for designing, constructing, and operating a UV fluid disinfection system that is nowhere taught or suggested in the prior art or mathematical models for predicting fluid disinfection and flow rates thereof.

Another preferred embodiment according to the present invention employs medium to high-pressure UV lamps, more preferably high-pressure UV lamps.

In one embodiment according to the present invention, the UV light source is a Fusion RF UV lamp, which is presently commercially available and supplied by Fusion UV Systems, Inc. The fusion lamp is a preferred lamp for a planar vertical riser system configuration, according to the present invention, to provide fast flow rates of the fluid treated within the system. This fusion lamp has a spectrum like a low-pressure lamp, having very strong UVB&C availability and output, but is a high power lamp having approximately 200W/cm. Significantly, as set forth in the foregoing, no prior art teaches or suggests the use of high pressure lamps, in fact, all standard formulas, including those developed by Dr. George Tchobanoglous, for system design and operation use low pressure lamps.

An additional advantage of high-power lamp systems is that extra-UV wavelengths, when delivered at sufficient intensity, may destroy or otherwise inactivate microorganisms as well. Several mechanisms of action are possible, but in general, the high-dose light denatures cell components such as proteins, cell membranes, and the like, and inactivates the microorganism.

The present invention advantageously includes all of the above features, in particular because the UV lamps are separated from the flow stream and include light delivery system that incorporates optical components. Without the use of optical components in combination with the UV light source, the intensity of the light could not be effectively focused, directed, and controlled to provide an efficacious disinfection because the UV dosage at the water surface and thereunder would not be great enough to sterilize the microorganisms.

However, the use of the vertical riser configuration creates even more surprising results in that a multiplicity of UV dose zones are created as the fluid to be treated is forced via a hydraulic system toward the UV light source system, including UV light source or lamp and optical component(s).

The present invention allows a significantly simplified system; potentially significantly lower operating costs, and the capacity to process large quantities of water as well as relatively small quantities, as for personal or in-home use. For an in-home system, as best illustrated in FIG. 2, a single vertical riser UV light source system, shown generally at 200, is constructed and configured to be attached to a water storage unit sized for a dwelling, between about twenty to about 100 gallons. In this system, the UV light source 310 is positioned within a UV light source system 300, including optical components as previously described, above the fluid to be treated and projecting a UV dose zone downward toward and into the fluid to be treated, with the fluid moving from the influent point 120, flowing vertically toward the UV light source, and then exits the effluent point 140. The at least one UV light source is positioned above the fluid to be treated and projecting UV light ray output 350 downward toward and into the fluid to be treated, with the fluid moving upward toward the UV light source. Several UV dose zones are established within the system. Several UV dose zones are established within the VRC system, generally shown as 500 in FIG. 6. The first zone is the light source system exit UV dose zone 510, which occurs at the light source system and air interface. Then next zone is the air/vapor UV dose zone 520, which occurs just beneath the UV light source and just above the water and the at least one interface plate 240. The next zone is the interface plate UV dose zone 530, which occurs at the intersection of the water and the at least one interface plate 240. The at least one interface plate is used to provide a reaction zone for UV disinfection above the fluid and to provide additional treatment means for balancing pH, affecting effluent chemistry, providing a catalyst, and the like. The last zone is the submerged UV dose zone 540, which creates a variable UV dose zone that decreases in effectiveness at greater distances from the UV light source.

FIG. 4 is an illustration of a side view of another embodiment of the present invention connected to a fluid reservoir and shown generally at 400. Notably, this reservoir-based UV light source for disinfection may be advantageously combined with the VRC system to ensure and guarantee the purity of the water exiting the overall system. However, particularly where the water contained within the reservoir or holding container has been pretreated or purified in previous steps, the addition of the VRC system may not be required as the non-VRC system constructed and configured to disinfect the static fluid within the reservoir or container may reasonably and adequately maintain the sterility and/or purity of the water.

Furthermore, the first aspect of the reservoir system is a fluid reservoir shown generally at 110. In this system, the UV light source 310 is positioned within a UV light source system 300, including optical components as previously described, above the fluid stored in the reservoir 110 and projecting a UV dose zone downward toward and into the fluid to be pre-treated. This reservoir fluid could be previously treated/purified or not. As set forth in the foregoing, where the water contained within the reservoir or holding container has been pre-treated or purified in previous steps, the addition of the VRC system may not be required as the non-VRC system constructed and configured to disinfect the static fluid within the reservoir or container adequately maintains the microbial purity of the water.

The at least one UV light assembly is positioned above the water to be disinfected or maintained at a disinfected state and projecting UV light ray output 350 downward toward and into the water. Once again, the light source system is provided in the reservoir system to prevent microorganism build-up in the reservoir. For completion of the system for applications where purity must be guaranteed, a single vertical riser UV light source system, shown generally at 200, is constructed and configured to be attached to the reservoir system 400. In this system, the UV light source 310 is positioned within a UV light source system 300, including optical components as previously described, above the fluid to be treated and projecting a UV dose zone downward toward and into the fluid to be treated, with the fluid moving from the influent point 120 (reservoir effluent point), flowing vertically toward the UV light source, and then exits the effluent point 140. The at least one UV light source is positioned above the fluid to be treated and projecting UV light ray output 350 downward toward and into the fluid to be treated, with the fluid moving upward toward the UV light source.

Several UV dose zones are established within the system, generally shown as 500 in FIG. 6. The first zone is the light source system exit UV dose zone 510, which occurs at the light source system and air interface. Then next zone is the air/vapor UV dose zone 520, which occurs just beneath the UV light source and just above the water and the at least one interface plate 240. The next zone is the interface plate UV dose zone 530, which occurs at the intersection of the water and the at least one interface plate 240. The at least one interface plate is used to provide a reaction zone for UV disinfection above the fluid and to provide additional treatment means for balancing pH, affecting effluent chemistry, providing a catalyst, and the like. The last zone is the submerged UV dose zone 540, which creates a variable UV dose zone that decreases in effectiveness at greater distances from the UV light source.

TEST EXAMPLE

This section outlines the results of a water disinfection test using the Non-Riser Configuration Home Disinfection System (NRC-HDS), as shown in FIG. 4. This example is not necessarily optimized, but a reduction to practice of a preferred embodiment and not a limitation on configuration. This example is illustrative of what can be done for a UV fluid disinfection system and method, wherein the fluid is water. The test example with results follows:

Test Example and Results—Non-Riser Configuration Home Disinfection System (NRC-HDS)

In this preferred embodiment according to the present invention of the home water purifier, a single spectral calibration lamp is used. An example of such a lamp is the ORIEL Instruments Hg (Ar) spectral calibration lamp model 6035. This lamp emits UV radiation at 254 nm. When operated at 15 mA using a DC power supply, this lamp is stated to emit 74 microwatt/cm2 of 254 nm wavelength light at 25 cm from the source. When operated at 18 mA, the lamp has a rated life of 5000 hours. The lamp is inserted via a threaded coupling into the top of a stainless steel tank. The stainless steel tank is cylindrical with a height of 61 cm and a diameter of 56 cm. The tank contains a vinyl spigot approximately 1 inch from the base, a ½ inch stainless steel plug in the center of the base, and a ½ inch stainless steel plug approximately 3 inches from the top. When filled with 125 liters of water, there are approximately 4 inches of clearance between the surface of the water and the top of the tank.

In a demonstration of the effectiveness of this preferred embodiment according to the present invention, the tank was sterilized with UV light, then filled with 125 liters of sterile, deionized water. The water was sterilized by UV irradiation for approximately 6 hours. After irradiation, the tank was allowed to ventilate until the odor of ozone had abated. Samples were taken of the water to demonstrate that no coliform CFUs were present prior to inoculation. Thereupon, 2 ml of a broth containing *E. Coli* at approximately $1.14 \times 10^5$/CFUs ml was added to the tank. The tank was agitated slowly for 3 hours with a magnetic stirring apparatus to disperse the bacteria. 100 ml and/or 10 ml samples were collected by filtration through 0.45 micrometer filters. After filtration, the filters were removed and placed in petri dishes containing an absorbent pad and approximately 2 ml of coliform indicator media. Petri dishes were then incubated overnight at approximately 37 degrees Centigrade. The tank was sampled periodically for 3 hours to determine if the bacteria were dispersed and the spontaneous death rate of the bacteria. The Hg (Ar) lamp was then turned on, and allowed to irradiate the tank contents for 24 hours. Samples were collected at 5 and 15 minutes after turning on the lamp, and every 15 minutes thereafter until 2 hours after turning on the lamp. Thereupon, samples were collected at 30 minute intervals for another 2 hours, and a final sample was collected at 8 hours. The results are present in Table 1 below. As can be seen from Table 1, after minutes irradiation, no CFUs were present in a 100 ml sample of water. Thus, after only 5 minutes of irradiation, this preferred embodiment of the invention was able to sterilize 125 liters of drinking water inoculated with approximately $2.3 \times 10^5$ CFUs of *E. coli*. Several factors, including the internal reflectance of the tank, are believed to have contributed to the surprising efficacy of this system.

TABLE 1

Results of UV Irradiation by preferred embodiment according to the present invention of water containing *E. coli*.[1]

| Timepoint (minutes) | UV | CFU count |
| --- | --- | --- |
| −30 | − | 840[2] |
| 0 | − | 710[2] |
| +5 | + | 0[3] |
| +15 | + | 0[3] |

[1]Approximately $2.3 \times 10^5$ CFUs of *E. coli* were added to 125 liters of sterile, deionized water and UV-irradiated for 24 hours with an ORIEL Instruments Model 6035 UV spectral calibration lamp.
[2]CFU counts detected in 10 ml of sampled water × 10.
[3]CFU counts in detected in 100 ml of sampled water.

The several advantages of this system include the fact that the non-submerged lamp does not require as extensive cleaning maintenance as a submerged lamp does to remove fouling.

Additionally, this intermittent-type system arrangement beneficially extends the lamp life thereby providing a longer replacement time or lamp life cycle. Since the lamp life is degraded by turning it off and on, the system can be constructed and configured to allow the reservoir to be significantly depleted before restarting the lamp (e.g., where a purified water reservoir or tank is used, the lamp activity can be controlled, preprogrammed, and otherwise regulated to correspond to the tank water size and water level. Depending on the size of the reservoir, and the number of people using the system (as measured in demanded or used gallons/day), the lamp is arranged, configured, and programmed to run intermittently, e.g., for an hour or so per day. In this way, a lamp continuous operation life of about a month could be extended to perhaps a year, depending upon the particular characteristics and specifications of the system, including water characteristics.

Thus, as can be seen from the advantages of this preferred embodiment according to the present invention over the prior art, the maintenance required for this preferred embodiment according to the present invention is significantly reduce with respect to the prior art.

The present invention requires some pretreatment of the water in cases of water with high turbidity prior to exposure to UV dose zones of the present invention. Traditional means for reducing turbidity including, but not limited to, filtration, dilution, reverse osmosis and chemical treatment may be advantageously employed to increase the UV efficacy of the system according to the present invention. However, certain aspects of the preferred embodiment allow it to more easily handle high turbidity fluids than the prior art.

The interface plate may induce turbulence or cause fluid cascade with a non-planar surface, stair-step surface, downwardly sloping surface, or other the like. The induction of turbulence is particularly advantageous when the fluid is turbid. Turbidity, which is the state of water when it is cloudy from having sediment stirred up, interferes with the transmission of UV energy and decreases the disinfection efficiency of the UV light disinfection system. Thus, turbulence, by inducing rotation in the particle, causes all aspects of a particle to be exposed to the UV light. Additionally, the photocatalytic properties of the system reduce turbidity by degrading the compounds or particles responsible for the turbidity. Furthermore, the reflective aspects of the surfaces of the system enhance the efficacy of the system when operated under turbid conditions because the UV light can strike the various aspects of a particle with the need for the particle to be rotating, thus overcoming the opacity of the particle. Another aspect that enhances performance under turbid conditions is the high UV light intensity of the system. The high UV light intensity can more easily compensate for fluctuations in turbidity than lower-intensity systems. Thus, the preferred embodiment has several characteristics that enhance its performance under turbid conditions.

In cases where the water has high iron or manganese content, is clouded and/or has organic impurities, it is usually necessary to pre-treat the water before it enters the UV disinfection stage because deposits on the quartz-encased submerged UV lamps, which are immersed in the water to be treated, interfere with the UV light transmission, thereby reducing the UV dose and rendering the system ineffective. Prior art typically employs UV purification in conjunction with carbon filtration, reverse osmosis and with certain chemicals to reduce fouling between cleanings of the quartz sleeves that surround the UV lamps. Thus, another advantage of the preferred embodiment is that turbidity reduction is not necessary for the system to perform adequately, and thus the system eliminates the need for expensive pre-treatment of the fluid to reduce turbidity.

The contribution of the reflectance of internal surfaces to the efficacy of the system can be capitalized upon by incorporating UV-reflective materials and reflection-enhance design into the reservoir. These same surfaces can also be manufactured such that they incorporate photocatalysts, as previously taught for the interface plate. Moreover, additional surfaces to support photocatalyst may be added to the reservoir or VRC system. Thus, an integrated design that incorporates UV-reflectant materials, UV-reflectant design, photocatalysts, and additional photocatalyst surfaces will greatly enhance the efficacy of the system.

Certain modifications and improvements will occur to those skilled in the art upon a reading of the foregoing description. By way of example, various optical components are used depending upon the particular UV light source or lamp selection for a given system. Also, a plurality of UV light source systems, either planar horizontal or retrofit configurations and/or cylindrical vertical riser configurations, are combined and arranged in series to increase the flow rates for which effective UV disinfection of the fluid occurs. Moreover, a wide range of fluid applications are contemplated within the scope of the present invention, including application of the UV fluid disinfectant system and method to the disinfection of other water containers, water sources, and water-dispensing devices, including, but not limited to, ambient temperature and chilled water tanks, refrigerators, water fountains, water towers, beverage makers, beverage dispensers, dishwashers, water heaters, washing machines, bathtubs, showers, toilets, and water pumps. Additionally, water storage devices that require potable water, but which water is not principally intended for drinking, may be fitted with a UV fluid disinfectant system and method according to the present invention. By way of example and not of limitation, swimming pools, hot tubs, steam rooms, saunas, water parks and ornamental water fountains may be fitted with a UV fluid disinfection system and method according to the present invention in order to disinfect or maintain the microbial purity of the water contained or utilized therein.

These multiple points of application may also be connected to a single light source, such as a light pump, by light guides. Such an arrangement would eliminate the need for a lamp or light source at every point of application. Because it may not be necessary to continuously irradiate each point of application, such an arrangement would allow the same size lamp as would be required for a single application to service multiple applications intermittently and/or on demand, thus utilizing the lamp more efficiently. Additionally, placing the lamp exterior to the tank reduces the risk of glass and/or mercury contaminating the water should the lamp or lamp housing break. An additional benefit to such a configuration is that filters previously required in immersion-type systems to prevent such contamination are no longer required.

All modifications and improvements have been deleted herein for the sake of conciseness and readability but are properly within the scope of the following claims.

We claim:

1. An ultraviolet disinfection (UV) system for treating drinking water, the system comprising at least one light source positioned within a housing and connected to a power source for producing a UV light output from the housing, the system including at least one optical component positioned between the at least one light source and the UV light output from the housing, thereby producing a focused, controllable UV light output that has at least one UV dose zone for providing effective sterilization of microorganisms within the water.

2. The UV system according to claim 1, wherein the at least one UV light source is one lamp.

3. The UV system according to claim 1, wherein the at least one UV light source is a UV lamp.

4. The UV system according to claim 3, wherein the at least one UV light source is a spectral calibration lamp.

5. The UV system according to claim 3, wherein the at least one UV light source is an electrodeless lamp.

6. The UV system according to claim 3, wherein the at least one UV light source is a mercury halide lamp.

7. The UV system according to claim 1, wherein the at least one UV light source is a light pump device.

8. The UV system according to claim 7, wherein the output from the at least one UV light source is distributed by fiber optic transmission lines.

9. The UV system according to claim 7 wherein the fiber optic transmission lines having a first end connected to the housing output such that the UV light output from the housing passes through the fiber optic transmission lines and exiting from a second end such that the UV light output exiting the fiber optic transmission lines is projected into the water.

10. The UV system according to claim 8, wherein the fiberoptic lines include acrylic fibers.

11. The UV system according to claim 8, wherein the fiberoptic lines include glass fibers.

12. The UV system according to claim 8, wherein the fiberoptic lines include liquid core fibers.

13. The UV system according to claim 8, wherein the fiberoptic lines include hollow core fibers.

14. The UV system according to claim 8, wherein the fiberoptic lines include core-sheath fibers.

15. The UV system according to claim 8, wherein at least one fluid-containing device is connected to the light pump device via fiberoptic transmission lines.

16. The UV system according to claim 1, further including a non-fouling lamp housing thereby eliminating cleaning of the lamp housing to ensure consistent UV disinfection of the fluid.

17. The UV system according to claim 1, wherein the light housing is affixed to a reservoir and the UV light output disinfects a substantially non-flowing water supply contained within the reservoir.

18. The UV system according to claim 17, wherein the system has a non-vertical riser configuration.

19. The UV system according to claim 1, wherein the lamp housing is affixed to a reservoir with flowing water contained therein.

20. The UV system according to claim 2, further including a vertical riser configuration (VRC) wherein the water is moved at a predetermined rate toward the UV light output thereby producing an increasing UV dose within the water as it approaches the light output.

21. The UV system according to claim 20, wherein an interface zone that is formed at the interface plate includes at least one additive that influence characteristics of the fluid as the fluid passes through the interface zone and over a surface zone that exists at a superior surface of the interface plate that is positioned closest to the UV light source.

22. The UV system according to claim 21, wherein the at least one additive is selected from the group consisting of $TiO_2$, $WO_2$, $ZnO$, $ZnS$, $SnO_2$, and $PtTiO_2$.

23. The UV system according to claim 20, wherein the vertical riser configuration system is portable.

24. The UV system according to claim 20, wherein the system is adaptable to be removably connected to a piping system for carrying water to an end user output, such that a multiplicity of systems may be positioned to function at a corresponding multiplicity of end user outputs to provide disinfected, purified water in many locations at once.

25. The UV system according to claim 1, wherein the at least one optical component is selected from the group consisting of reflectors, shutters, lenses, splitters, splitting reflectors, cascading reflectors, focalizers, mirrors, rigid and flexible light guides, homogenizer, mixing rods, manifolds and other couplers, filters, gratings, diffracters, color wheels and fiber optic transmission lines.

26. The UV system according to claim 1, wherein the at least one optical component is an off-axis optical component.

27. The UV system according to claim 1, wherein the at least one optical component is a gradient component.

28. The UV system according to claim 1, wherein the at least one optical component is UV transmissive.

29. The UV system according to claim 1, wherein the at least one optical component is UV reflective.

30. The UV system according to claim 1 wherein the at least one optical component includes fiber optic transmission lines having a first end connected to the housing output such that the UV light output from the housing passes through the fiber optic transmission lines and exiting from a second end such that the UV light output exiting the fiber optic transmission lines is projected into the water.

31. The UV system according to claim 25, wherein the at least one optical component is a lens for focusing light from the light source through an output point in the housing and into the water for disinfection thereof.

32. The UV system according to claim 31, wherein the lens is a parabolic lens.

33. The UV system according to claim 1, wherein the at least one UV dose zone includes a water-air interface dose zone and a variable intra-fluid dose zone.

34. The UV system according to claim 1, wherein the at least one UV light source is positioned outside the water to be treated thereby providing effective sterilization of microorganisms within the water.

35. An ultraviolet disinfection (UV) system for treating drinking water, the system comprising at least one light source positioned outside the water to be treated and positioned within a housing and connected to a power source for producing a UV light output from the housing, the system including at least one optical component positioned between the at least one light source and the UV light output from the housing, thereby producing a focused, controllable UV light output that has at least one UV dose zone for providing effective sterilization of microorganisms within the water.

36. The UV system according to claim 35, wherein the at least one UV light source is a single UV lamp.

37. The UV system according to claim 35, wherein the at least one UV light source is a spectral calibration lamp.

38. The UV system according to claim 35, wherein the at least one UV light source is an electrodeless lamp.

39. The UV system according to claim 35, wherein the at least one UV light source is a mercury halide lamp.

40. The UV system according to claim 35, wherein the at least one UV light source is a light pump device.

41. The UV system according to claim 35, wherein the at least one UV light source is a pulsed lamp device.

42. The UV system according to claim 35, further including a non-fouling lamp housing thereby eliminating cleaning of the lamp housing to ensure consistent UV disinfection of the fluid.

43. The UV system according to claim 35, wherein the light housing is affixed to a reservoir and the UV light output disinfects a substantially non-flowing water supply contained within the reservoir.

44. The UV system according to claim 35, wherein the lamp housing is affixed to a reservoir with flowing water contained therein.

45. The UV system according to claim 35, further including a timer for automatically activating and deactivating the light source at a predetermined time.

46. The UV system according to claim 35, further including a vertical riser configuration (VRC) wherein the water is moved at a predetermined rate toward the UV light output thereby producing an increasing UV dose within the water as it approaches the light output.

47. The UV system according to claim 35, wherein an interface zone that is formed at the interface plate includes at least one additive that influence characteristics of the water as the water passes through the interface zone and over a surface zone that exists at a superior surface of the interface plate that is positioned closest to the UV light source.

48. The UV system according to claim 47, wherein the at least one additive is selected from the group consisting of $TiO_2$, $WO_2$, $ZnO$, $ZnS$, $SnO_2$, and $PtTiO_2$.

49. The UV system according to claim 45, wherein the system is adaptable to be removably connected to a piping system for carrying water to an end user output, such that a multiplicity of systems may be positioned to function at a corresponding multiplicity of end user outputs to provide disinfected, purified water in many locations at once.

50. The UV system according to claim 35, wherein the at least one optical component is selected from the group consisting of reflectors, shutters, lenses, splitters, splitting reflectors, cascading reflectors, focalizers, mirrors, rigid and flexible light guides, homogenizer or mixing rods, manifolds and other couplers, filters, gratings, diffracters, color wheels and fiber optic transmission lines.

51. The UV system according to claim 35, wherein at least one optical component is UV transmissive.

52. The UV system according to claim 35, wherein at least one optical component is UV reflective.

53. The UV system according to claim 35, wherein the at least one optical component includes fiber optic transmission lines having a first end connected to the housing output such that the UV light output from the housing passes through the fiber optic transmission lines and exiting from a second end such that the UV light output exiting the fiber optic transmission lines is projected into the water.

54. The UV system according to claim 53, wherein the fiberoptic lines include acrylic fibers.

55. The UV system according to claim 53, wherein the fiberoptic lines include glass fibers.

56. The UV system according to claim 53, wherein the fiberoptic lines include liquid core fibers.

57. The UV system according to claim 53, wherein the fiberoptic lines include hollow core fibers.

58. The UV system according to claim 53, wherein the fiberoptic lines include core-sheath fibers.

59. The UV system according to claim 50, wherein the at least one optical component is a lens for focusing light from the light source through an output point in the housing and into the water for disinfection thereof.

60. The UV system according to claim 59, wherein the lens is a parabolic lens.

61. The UV system according to claim 35, wherein the at least one UV dose zone includes a water-air interface dose zone and a variable intra-fluid dose zone.

62. A method for purifying drinking water comprising the steps of:

providing a UV purification system comprising at least one UV light source outside the drinking water to be treated and at least one interface zone established between the at least one UV light source and the water to be treated, the at least one UV light source designed, configured, and connected to produce UV light creating at least one UV dose-zone outside the water;

presenting a surface zone on the at least one interface zone, wherein the surface zone has a UV dose zone associated therewith for disinfecting the water to be treated;

introducing water into the system, the water passing through the at least one UV dose zone within the water and passing through the at least one interface zone and surface zone UV dose zone;

disinfecting the water via exposure to the UV light in the UV dose zones;

dispensing the disinfected water outside the system.

63. The method according to claim 62, further including the step of forcing water via a hydraulic system through a vertical riser configuration of the system.

64. The method according to claim 62, further including the step of modifying the water characteristics via at least on e additive on the interface zone causing a reaction in the fluid.

65. The method according to claim 62, further including the step of introducing turbulence in the water as the water passes throughout the system , thereby increasing the exposure to UV light and disinfection thereby.

66. The method according to claim 62, further including the step of introducing a catalyst at the interface zone.

67. The method according to claim 62, wherein the system includes a non-submerged light source.

68. A method for providing ultraviolet disinfection (UV) of drinking water, the method comprising the steps of:

providing a UV purification system comprising at least one UV light source coupled with at least one UV-transmissive optical component outside the water to be treated and at least one interface zone positioned between the at least one UV light source and the water to be treated, the at least one UV light source designed, configured, and connected to produce UV light creating at least one UV dose zone outside the water;

presenting a surface zone on the at least one interface zone, wherein the surface zone has a UV dose zone associated therewith for disinfecting the water to be treated;

introducing water into the system, the water passing through the at least one UV dose zone within the water and passing through the at least one interface zone and surface zone UV dose zone;

disinfecting the water via exposure to the UV light in the UV dose zones;

dispensing the disinfected water outside the system.

69. The method according to claim 68, further including the step of forcing water via a hydraulic system through a vertical riser configuration of the system.

70. The method according to claim 68, further including the step of modifying the water characteristics via at least one additive on the interface zone causing a reaction in the water.

71. The method according to claim 68, further including the step of introducing turbulence in the water as the water passes throughout the system, thereby increasing the exposure to UV light and disinfection thereby.

72. The method according to claim 68, further including the step of introducing a catalyst at the interface zone.

* * * * *